(12) United States Patent
Otsuki et al.

(10) Patent No.: US 11,929,173 B2
(45) Date of Patent: Mar. 12, 2024

(54) LEARNING APPARATUS, REHABILITATION SUPPORT SYSTEM, METHOD, PROGRAM, AND TRAINED MODEL

(71) Applicant: Toyota Jidosha Kabushiki Kaisha, Toyota (JP)

(72) Inventors: Nobuhisa Otsuki, Toyota (JP); Ai Kurokawa, Toyota (JP); Issei Nakashima, Toyota (JP); Manabu Yamamoto, Toyota (JP); Taiga Matsumoto, Nagoya (JP); Hiroaki Daba, Nisshin (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 926 days.

(21) Appl. No.: 16/916,545

(22) Filed: Jun. 30, 2020

(65) Prior Publication Data

US 2021/0005319 A1   Jan. 7, 2021

(30) Foreign Application Priority Data

Jul. 1, 2019 (JP) .................................. 2019-122897

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/0022* (2013.01); *A61B 5/1121* (2013.01); *A61B 5/16* (2013.01);
(Continued)

(58) Field of Classification Search
CPC ........ G16H 50/20; G16H 10/60; G16H 20/30; G16H 40/40; G16H 40/67; G16H 50/30;
(Continued)

(56) References Cited

U.S. PATENT DOCUMENTS 10,130,311 B1 * 11/2018 De Sapio ............. A61B 5/7455
2015/0342820 A1   12/2015 Shimada et al.
2018/0344562 A1 * 12/2018 Komatsu ................ A61H 1/024

FOREIGN PATENT DOCUMENTS

JP   2015-008960 A   1/2015
JP   2015-159935 A   9/2015
(Continued)

*Primary Examiner* — Joy Chng
(74) *Attorney, Agent, or Firm* — Dinsmore & Shohl LLP

(57) ABSTRACT

The server is a learning apparatus including a data acquisition unit and a learning unit. The data acquisition unit acquires profile data and a selected assistance level as learning data. The profile data indicates a profile related to a trainee before executing rehabilitation regarding rehabilitation executed using a walking training apparatus as a rehabilitation support system. The selected assistance level is an assistance level selected at the time of executing the rehabilitation. The learning unit learns to determine a recommended assistance level recommended to be selected when the trainee uses the rehabilitation support system based on the learning data. Further, the learning unit generates a trained model that receives the profile data and outputs the recommended assistance level based on the learning.

12 Claims, 12 Drawing Sheets

(51) Int. Cl.
  *A61B 5/11*   (2006.01)
  *A61B 5/16*   (2006.01)
  *A61H 3/00*   (2006.01)
  *A63B 22/02*  (2006.01)
  *G16H 10/60*  (2018.01)
  *G16H 20/30*  (2018.01)
  *G16H 40/40*  (2018.01)
  *G16H 40/67*  (2018.01)
  *G16H 50/30*  (2018.01)
  *G16H 50/50*  (2018.01)

(52) U.S. Cl.
  CPC .......... *A61B 5/4064* (2013.01); *A61B 5/4585* (2013.01); *A61B 5/4842* (2013.01); *A61B 5/7267* (2013.01); *A61H 3/00* (2013.01); *A63B 22/02* (2013.01); *G16H 10/60* (2018.01); *G16H 20/30* (2018.01); *G16H 40/40* (2018.01); *G16H 40/67* (2018.01); *G16H 50/30* (2018.01); *G16H 50/50* (2018.01); *A61H 2003/007* (2013.01); *A61H 2205/088* (2013.01); *A61H 2205/102* (2013.01); *A61H 2205/106* (2013.01)

(58) Field of Classification Search
  CPC ..... G16H 50/50; A61B 5/0022; A61B 5/1121; A61B 5/16; A61B 5/4064; A61B 5/4585; A61B 5/4842; A61B 5/7267; A61B 5/1124; A61B 5/4082; A61B 5/4848; A61B 2505/09; A61B 2562/0219; A61H 3/00; A61H 2003/007; A61H 2205/088; A61H 2205/102; A61H 2205/106; A61H 1/00; A63B 22/02; G06N 3/044; G06N 3/045; G06N 20/00
  USPC ........................................................ 705/2–3
  See application file for complete search history.

(56) References Cited

FOREIGN PATENT DOCUMENTS

| | | | |
|---|---|---|---|
| JP | 2015-223294 A | 12/2015 | |
| JP | 2018-114278 A | 7/2018 | |
| WO | 2019/116093 A1 | 6/2019 | |
| WO | WO-2019116093 A1 * | 6/2019 | ............ A61H 1/024 |

* cited by examiner

| DATA SET No. | PARAMETER 1 WALKING FIM | PARAMETER 2 SIAS | PARAMETER 3 DISEASE TYPE | PARAMETER 4 RECOVERY HISTORY | TEACHER DATA ASSISTANCE LEVEL |
|---|---|---|---|---|---|
| 1 | 2 | 3 | CEREBRAL INFARCTION2 | C | 2 |
| 2 | 1 | 2 | CEREBRAL HEMORRHAGE3 | A | 5 |
| 3 | 7 | 6 | CEREBRAL INFARCTION1 | F | 1 |
| ... | ... | ... | ... | ... | ... |

Fig. 10

LEARNING APPARATUS, REHABILITATION SUPPORT SYSTEM, METHOD, PROGRAM, AND TRAINED MODEL

CROSS REFERENCE TO RELATED APPLICATIONS

This application is based upon and claims the benefit of priority from Japanese patent application No. 2019-122897, filed on Jul. 1, 2019, the disclosure of which is incorporated herein in its entirety by reference.

BACKGROUND

The present disclosure relates to a learning apparatus, a rehabilitation support system, a method, a program, and a trained model.

Trainees such as patients may use a rehabilitation support system such as a walking training apparatus when they perform rehabilitation. As an example of the walking training apparatus, Japanese Unexamined Patent Application Publication No. 2015-223294 discloses a walking training apparatus including a walking assistance apparatus that is attached to a leg of a trainee and assists the trainee in walking. The walking assistance apparatus includes a motor unit, and assists the trainee to walk by rotationally driving his/her knee joint according to the trainee's walking motion.

In some rehabilitation support systems, when a trainee performs rehabilitation, a training staff member such as a doctor or a Physical Therapist (PT) may attend the rehabilitation as an assistant for the trainee, and perform a setting operation for the rehabilitation support system.

SUMMARY

In order to perform an effective training which enables a trainee to recover in a rehabilitation support system, it is important to appropriately set a level of an assistance operation (assistance level) at the time of assisting a motion of the trainee according to the trainee's state. The assistance level is often set by a training staff member. However, the assistance level setting greatly depends on an experience or intuition of the training staff member. Thus, the effect of the training may differ depends on the training staff member who is responsible for the training.

The present disclosure has been made to solve such a problem. An object of the present disclosure is to provide a learning apparatus and the like for setting an appropriate assistance level.

A first example aspect of the present disclosure is a learning apparatus including a data acquisition unit and a learning unit. The data acquisition unit acquires profile data and a selected assistance level as learning data. The profile data indicates a profile related to a trainee before execution of the rehabilitation in regard to rehabilitation executed using a rehabilitation support system including an assistance apparatus for assisting a motion of the trainee. The selected assistance level is an assistance level of the assistance apparatus selected at the time of the execution of the rehabilitation. The learning unit learns to determine a recommended assistance level based on the learning data. The recommended assistance level is an assistance level of the assistance apparatus recommended to be selected when the trainee uses the rehabilitation support system. Further, the learning unit generates a trained model that receives the profile data and outputs the recommended assistance level based on the learning.

Then, the learning apparatus can generate a trained model that receives arbitrary profile data and outputs the assistance level recommended for the arbitrary profile data.

In the above learning apparatus, the learning unit may include an input layer acquisition unit that acquires the profile data as an input layer and a teacher data acquisition unit for acquiring the selected assistance level as teacher data of an output layer. This enables the learning apparatus to perform supervised learning by using the acquired profile data and the selected assistance level.

In the above learning apparatus, the data acquisition unit is configured to acquire, as the profile data, at least one item of data of: information about a type of a disease the trainee is suffering from; a cognitive level based on a functional independence measure of the trainee; an assessment score based on a stroke impairment assessment set of the trainee; an exercise ability level based on an exercise ability evaluation of the trainee; and history data indicating a history of the trainee's degree of recovery. Then, it is possible for the learning apparatus to output a recommended assistance level suitable for untrained profile data.

In the above learning apparatus, a type of the disease included in the profile data may be a brain disease of the trainee, and information related to the type of the disease may be information corresponding to a part of a brain damaged by the brain disease. Then, it is possible for the learning apparatus to output a recommended assistance level suitable for a part of a brain damaged by the brain disease the trainee is suffering from.

In the above learning apparatus, the assistance apparatus may be a motor for assisting the trainee to walk, and the assistance level may be an index indicating a magnitude of a torque of the motor. Further, in the above learning apparatus, the assistance apparatus may be a motor for assisting an extending motion of a knee joint of the trainee, and the assistance level may be an index indicating a magnitude of a torque of the motor with respect to a magnitude of an angle of the knee joint. Then, the learning apparatus can output a recommended assistance level suitable for walking training.

Another example aspect of the present disclosure is a rehabilitation support system capable of accessing a trained model that is a learning model generated by the above-described learning apparatus. The rehabilitation support system includes an output unit and a notification unit. The output unit is configured to output the profile data of the trainee as an input to the trained model. The notification unit is configured to notify a user of the rehabilitation support system of the recommended assistance level output from the trained model as a response to the input profile data. The rehabilitation support system according to the example aspect of the present disclosure may further include a server apparatus communicably connected to the rehabilitation support system. The server apparatus may include a storage unit configured to store the trained model. Then, the rehabilitation support system can notify a training staff member such as a PT of the recommended assistance level for the trainee who performs rehabilitation.

Another example aspect of the present disclosure is a learning method including a data acquisition step and a learning step. In the data acquisition step, profile data and a selected assistance level are acquired. The profile data indicates a profile of a trainee before execution of rehabilitation in regard to rehabilitation executed using a rehabilitation support system including an assistance apparatus for assisting a motion of a trainee. The selected assistance level is an assistance level of an assistance apparatus selected at the time of the execution of the rehabilitation. In the learning step, a recommended assistance level is learned to be determined based on the profile data and the selected assistance level. The recommended assistance level is an assistance level of the assistance apparatus recommended to be selected when the trainee uses the rehabilitation support system. The trained model generation step generates a trained model that receives the profile data and outputs the recommended assistance level based on the learning. In this manner, the learning method can generate a trained model that receives arbitrary profile data and outputs the assistance level recommended for the arbitrary profile data.

An example aspect of the present disclosure is a rehabilitation support method capable of accessing a trained model that is a learning model learned by the above-described learning method. The rehabilitation support method includes an output step of outputting the profile data of the trainee who uses the rehabilitation support system as an input to the trained model. The rehabilitation support method further includes a notification step of notifying a user of the rehabilitation support system of the recommended assistance level output from the trained model as a response to the input profile data. Then, the rehabilitation support system can notify a training staff member such as a PT of a recommended assistance level of the trainee who performs rehabilitation.

Another example aspect of the present disclosure is a learning program that causes a computer to execute a learning program including a data acquisition step, a learning step, and a trained model generation step. In the data acquisition step, profile data and a selected assistance level are acquired. The profile data indicates a profile of a trainee before execution of rehabilitation in regard to rehabilitation executed using a rehabilitation support system including an assistance apparatus for assisting a motion of a trainee. The selected assistance level is an assistance level of the assistance apparatus selected at the time of the execution of the rehabilitation. In the learning step, a recommended assistance level is learned to be determined. The recommended assistance level is the assistance level of the assistance apparatus recommended to be selected when the trainee uses the rehabilitation support system based on the profile data and the selected assistance level. In the trained model generation step, a trained model for receiving the profile data and outputting the recommended assistance level is generated based on the learning. Then, the learning program can generate a trained model that receives arbitrary profile data and outputs a recommended assistance level for the arbitrary profile data.

Another example aspect of the present disclosure is a trained model that is a learning model generated by the learning apparatus for causing a computer to function in such a way that the recommended assistance level is output based on the profile data of the trainee. By using this trained model, it is possible to output a recommended assistance level suitable for untrained profile data.

According to the present disclosure, it is possible to provide a learning apparatus and the like for setting an appropriate assistance level.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 10 shows an example of data to be input to the learning apparatus;

DETAILED DESCRIPTION

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem. Note that the same elements are denoted by the same reference signs throughout the drawings, and repeated description is omitted as necessary.

Embodiment

An embodiment will be described hereinafter with reference to the drawings.
(System Configuration)

Figure 1:
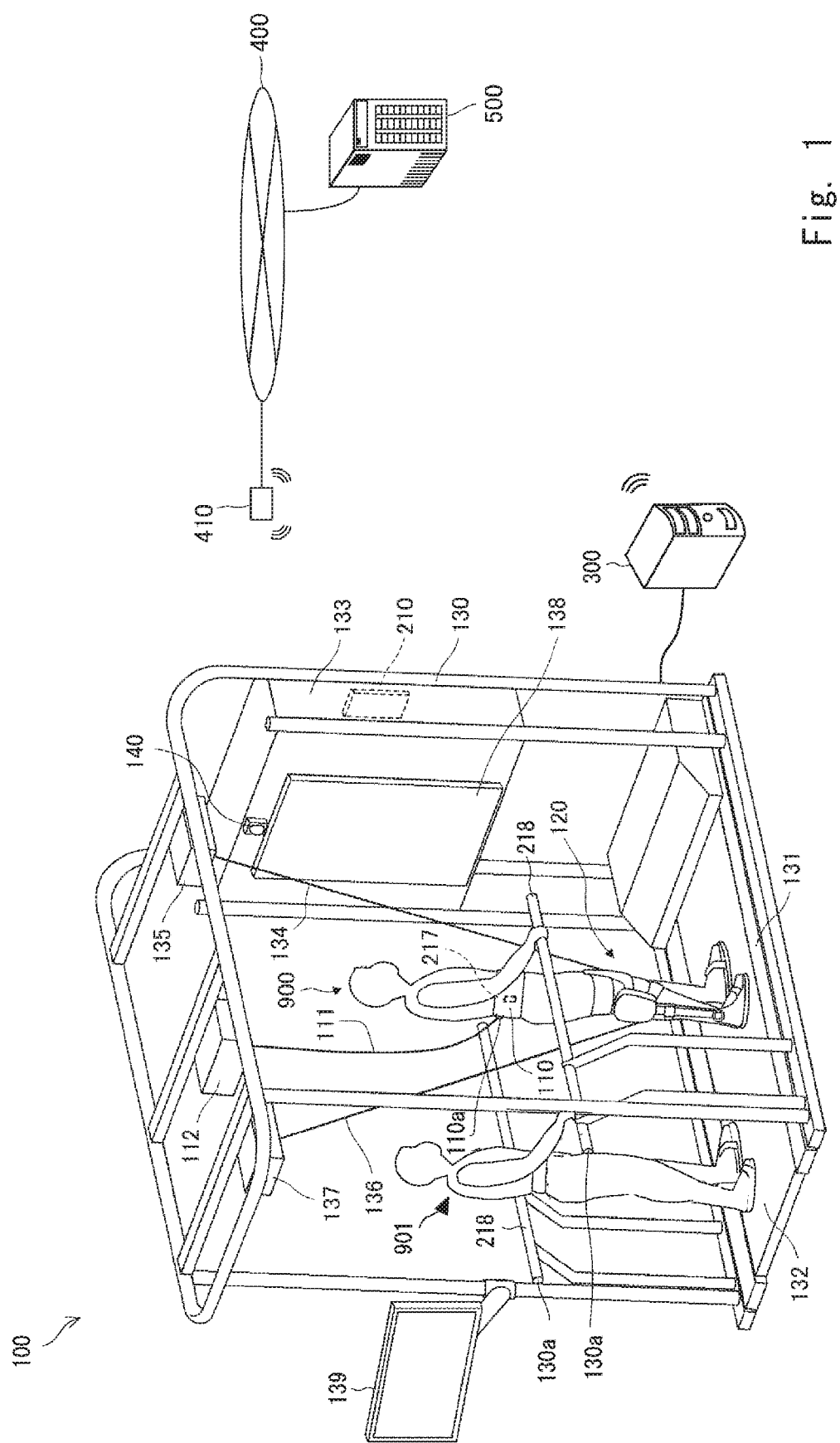
FIG. 1 is a schematic perspective view showing a rehabilitation support system according to an embodiment.

FIG. 1 is a general concept diagram showing an example of a configuration of a rehabilitation support system according to an embodiment. The rehabilitation support system (the rehabilitation system) according to this embodiment mainly includes a walking training apparatus 100, an external communication apparatus 300, and a server (a server apparatus) 500.

The walking training apparatus 100 is a specific example of a rehabilitation support system that supports rehabilitation performed by a trainee (a user) 900. The walking training apparatus 100 is an apparatus by which the trainee 900, who is, for example, a hemiplegic patient suffering from paralysis in one of his/her legs, does walking training under the guidance of a training staff member 901. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like.

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900. In addition to these components, the walking training apparatus 100 further includes a fall-prevention harness apparatus as a safety apparatus.

The frame 130 is disposed in a standing position on the treadmill 131 mounted on the floor surface. The treadmill 131 rotates a ring-shaped belt 132 by using a motor (not shown). The treadmill 131 is an apparatus that prompts the trainee 900 to walk, and the trainee 900, who does a walking training, gets on the belt 132 and tries walking in accordance with the movement of the belt 132. Note that the training staff member 901 can stand on the belt 132 behind the trainee 900 and walk together as shown in FIG. 1. However, the training staff member 901 may typically be in a state in which he/she can easily assists the trainee 900 such as standing with his/her feet on both sides of the belt 132.

The frame 130 supports, for example, the control panel 133 that houses an overall control unit 210 that controls motors and sensors, and a training monitor 138 that is formed by, for example, a liquid-crystal panel and shows progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the left and right sides of the trainee 900. Each of the handrails 130a is orientated in a direction parallel to the walking direction of the trainee 900. The vertical position and the left/right position of the handrails 130a are adjustable. That is, the handrails 130a may include a mechanism for changing its height. Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load (e.g., a pressure) received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

The camera 140 functions as an image pickup unit for observing the whole body of the trainee 900. The camera 140 is disposed near the training monitor 138 and positioned so as to face the trainee. The camera 140 takes still images and moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

By the coordinated operation of the front pulling unit 135 and the rear pulling unit 137, the load of the walking assistance apparatus 120 is cancelled so that it does not become a load on the diseased leg. Further, the swinging motion of the diseased leg is assisted according to the set level.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is cancelled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is cancelled.

The fall-prevention harness apparatus includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). By the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed over its surface. The management monitor 139 displays various menu items related to the training setting, various parameter values during the training, training results, and so on.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load (e.g., the pressure) on the sole of the foot, and outputs various data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

In this embodiment, the terms "leg" and "leg part" are used to refer to the entire part of the leg below the hip joint, and the terms "foot" and "foot part" are used to refer to a part of the leg from the ankle to the toe.

The overall control unit 210 generates profile data including various information about the trainee when the trainee performs training. The profile data may include, for example, symptom information of a disease that the trainee is suffering from, a cognitive level based on a functional independence measure, an assessment score based on a stroke impairment assessment set, an exercise ability level based on an exercise ability evaluation of the trainee, data indicating the degree of recovery, and data indicating attributes of the trainee. Details of the profile data will be described later.

The overall control unit 210 can also generate data other than the above-described profile data related to rehabilitation (hereinafter referred to as rehabilitation data). The details of the rehabilitation data will be described later.

The external communication apparatus 300 is a specific example of transmission means for transmitting the profile data and the rehabilitation data to the outside. The external communication apparatus 300 may have a function of receiving and temporarily storing data output from the walking training apparatus 100 and a function of transmitting the stored data to the server 500.

The external communication apparatus 300 is connected to the control panel 133 of the walking training apparatus 100 through, for example, a USB (Universal Serial Bus) cable. Further, the external communication apparatus 300 is connected to a network 400 such as the Internet or an intranet through a wireless communication apparatus 410 by, for example, a wireless LAN (Local Area Network). Note that the walking training apparatus 100 may be equipped with a communication apparatus instead of using the external communication apparatus 300.

The server 500 is a specific example of the information processing means for receiving the profile data and processing the received profile data. The server 500 is connected to the network 400 and has a function of accumulating profile data received from the external communication apparatus 300. The function of the server 500 will be described later.

In this embodiment, the walking training apparatus 100 is described as an example of the rehabilitation support system. However, the rehabilitation support system is not limited to this example and may be an arbitrary walking training system that supports rehabilitation performed by a trainee. For example, the rehabilitation support system may be an upper-limb rehabilitation support system that supports rehabilitation of a shoulder(s) or an arm(s). Alternatively, the rehabilitation support system may be a rehabilitation support system that supports rehabilitation for a balancing ability of a trainee.

Figure 2:
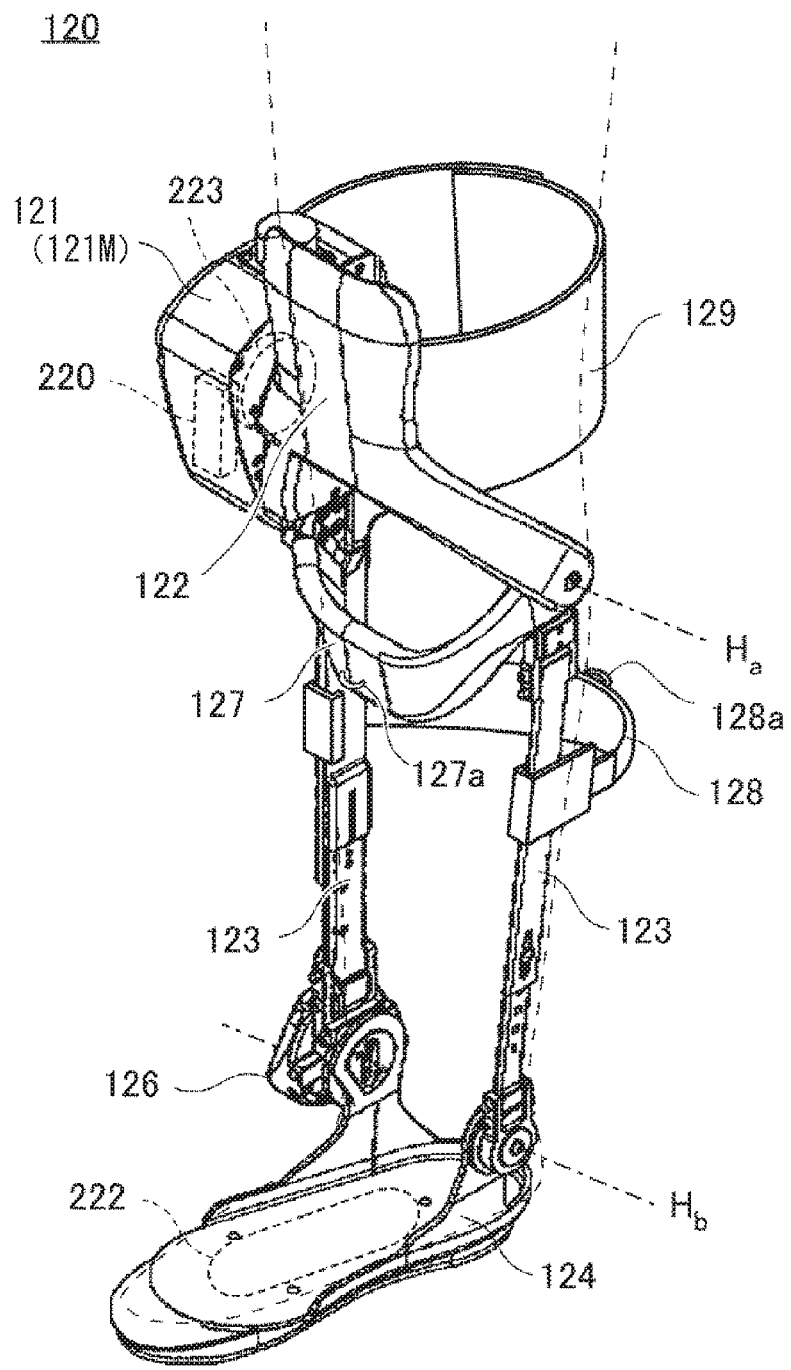
FIG. 2 is a schematic perspective view showing a walking assistance apparatus.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of a diseased leg, and a load sensor 222 for detecting a load (e.g., a pressure) applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, includes an upper-leg frame 122 and a lower-leg frame 123 rotatably connected to the upper-leg frame 122. Further, the frames also include a sole frame 124 rotatably connected to the lower-leg frame 123, a front connection frame 127 for connecting a front wire 134, and a rear connection frame 128 for connecting a rear wire 136.

The upper-leg frame 122 and the lower-leg frame 123 rotate relative to each other around a hinge axis $H_a$ shown in the figure. A motor 121M of the control unit 121 rotates according to an instruction from the assistance control unit 220, and by doing so, force the upper-leg frame 122 and the lower-leg frame 123 to open relative to each other around the hinge axis $H_a$ or force them to close relative to each other. The angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the figure. The angular range of their relative rotation is adjusted in advance by an adjustment mechanism 126.

The front connection frame 127 is disposed so as to extend in the left/right direction in front of the upper leg and is connected to the upper-leg frame 122 at both ends. Further, a connection hook 127a for connecting the front wire 134 is provided at or near the center of the front connection frame 127 in the left/right direction. The rear connection frame 128 is disposed so as to extend in the left/right direction behind the lower leg and is connected to the lower-leg frame 123 at both ends. Further, a connection hook 128a for connecting the rear wire 136 is provided at or near the center of the rear connection frame 128 in the left/right direction.

The upper-leg frame 122 includes an upper-leg belt 129. The upper-leg belt 129 is a belt integrally provided in the upper-leg frame and is wound around the upper leg of the diseased leg to fix the upper-leg frame 122 to the upper leg. In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load (e.g., a vertical pressure) received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
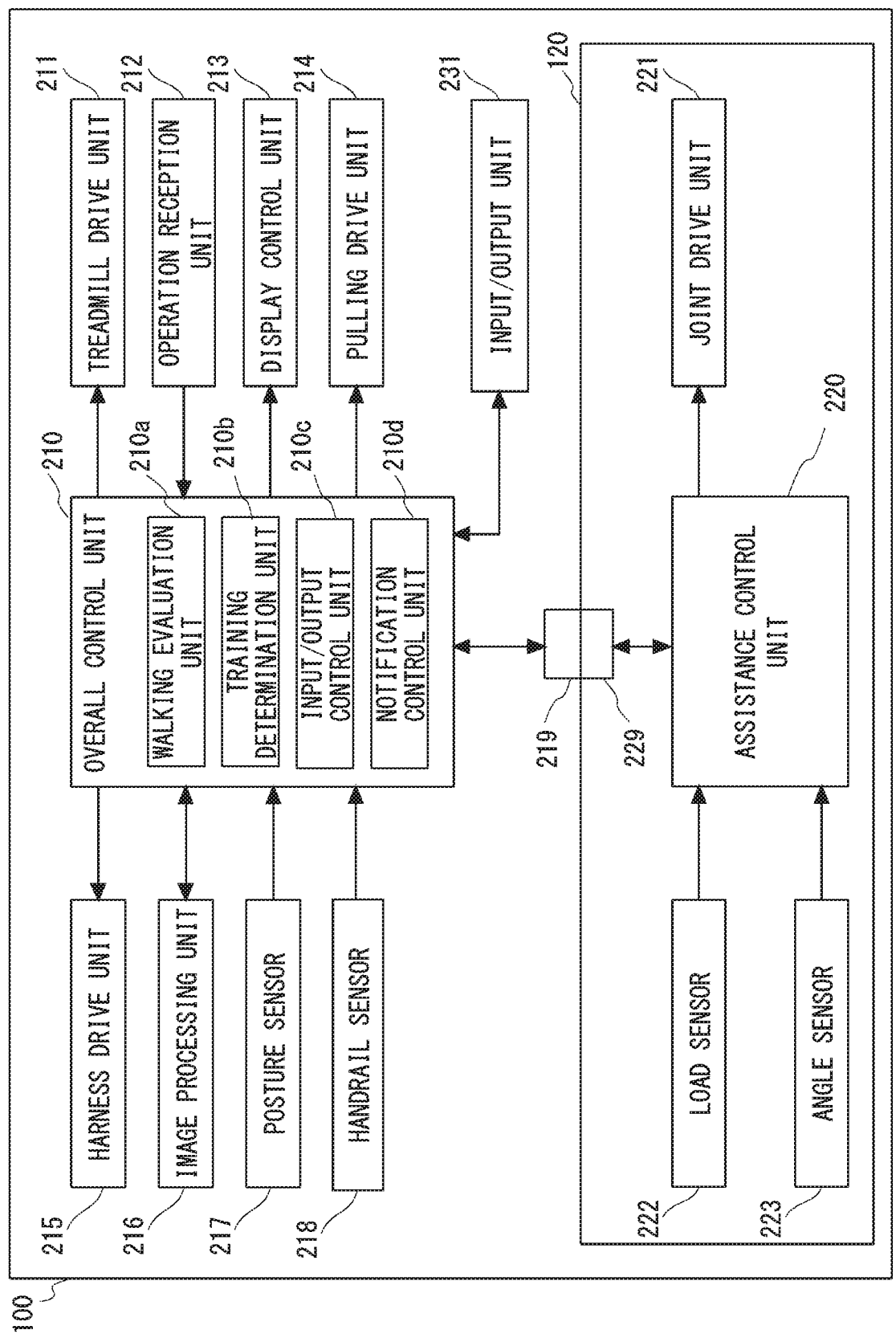
FIG. 3 is a block diagram showing a system configuration of the rehabilitation support system.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input/output unit 231, and a walking assistance apparatus 120.

The overall control unit 210 is, for example, an MPU (Micro Processing Unit) and controls the overall operations of the apparatus by executing a control program loaded from a system memory. The overall control unit 210 may include a walking evaluation unit 210a, a training determination unit 210b, an input/output control unit 210c, and a notification control unit 210d, all of which will be described later.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed over the management monitor 139, an accessory remote controller, etc., which constitute the operation reception unit 212. By the above-described operation, the training staff member can turn on/off the power, provide an instruction to start training, enter a numerical value for the setting, and select a menu item. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing progress of the training and a real-time video image shot by the camera 140.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies (i.e., determines), for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal.

Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load (e.g., a pressure) applied to the handrail 130a. That is, the amount of the load corresponding to the part of the trainee's own weight that the trainee 900 cannot support by both legs is applied to the handrails 130a. The handrail sensor 218 detects this load and transmits a detection signal to the overall control unit 210.

The overall control unit 210 also serves as a function execution unit that performs various arithmetic operations and controls related to the overall control. The walking evaluation unit 210a evaluates whether the walking motion of the trainee 900 is abnormal or not by using data acquired from various sensors. The training determination unit 210b determines a training result of a series of walking trainings based on, for example, a cumulative number of the abnormal walking evaluated by the walking evaluation unit 210a. The overall control unit 210 can generate, as part of the rehabilitation data, a result of this determination or the cumulative number of the abnormal walking, based on which the determination result has been obtained.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program supplied from the overall control unit 210. Further, the assistance control unit 220 notifies the overall control unit 210 of the state of the walking assistance apparatus 120 through the communication connection IFs 229 and 219. Further, the assistance control unit 220 performs control of walking assistance apparatus 120, such as the start/stop thereof, in response to a command from the overall control unit 210.

The joint drive unit 221 includes the motor 121M of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling.

The joint drive unit 221 can switch a driving force of the motor 121M of the control unit 121 to preset levels. The switching of the driving force of the motor 121M in the control unit 121 is set as an assistance level. That is, the assistance level in this embodiment indicates the strength of an assistance operation performed for the trainee 900 performing walking training. Details of the assistance level will be described later.

The load sensor 222 detects the magnitude and the distribution of the vertical load (e.g., the vertical pressure) applied to the sole of the trainee 900 and transmits a detection signal to the assistance control unit 220 as described above. The assistance control unit 220 can receive and analyze the detection signal, and thereby determines the swing/stance state.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle of the knee joint.

The input/output unit 231 includes, for example, a USB (Universal Serial Bus) interface and is a communication interface for connecting to an external apparatus (an external communication apparatus 300 or other external apparatus). The input/output control unit 210c of the overall control unit 210 communicates with the external apparatus through the input/output unit 231, rewrites the above-described control program stored in the overall control unit 210 and the control program stored in the assistance control unit 220, receives commands, outputs generated rehabilitation data, and so on. The walking training apparatus 100 communicates with the server 500 through the input/output unit 231 and the external communication apparatus 300 under the control of the input/output control unit 210c. For example, the input/output control unit 210c can control the transmission of rehabilitation data to the server 500 and the reception of a command from the server 500 through the input/output unit 231 and the external communication apparatus 300.

When it is necessary to provide a notification to the training staff member 901, the notification control unit 210d provides the notification from the management monitor 139 or a separately-provided speaker(s) by controlling the display control unit 213 or a separately-provided sound control unit or the like. The aforementioned situation where it is necessary to provide a notification to the training staff member 901 may be a situation where a command for providing a notification is received from the server 500. Details of this notification will be described later.

Next, the server 500 will be described in detail. The server 500 receives the profile data from the walking training apparatus 100 through the network 400 and then processes the received profile data. The server 500 uses a previously stored trained model when processing the profile data. The trained model is generated by performing machine learning using a plurality of teacher data pieces. The server 500 uses the trained model to determine a recommended assistance level from the received profile data. The server 500 transmits an assistance level as a processing result to the walking training apparatus 100 through the network 400. The server 500 may be configured to receive a plurality of profile data pieces from a plurality of walking training apparatuses 100. This allows the server 500 to collect a large amount of profile data.

Figure 4:
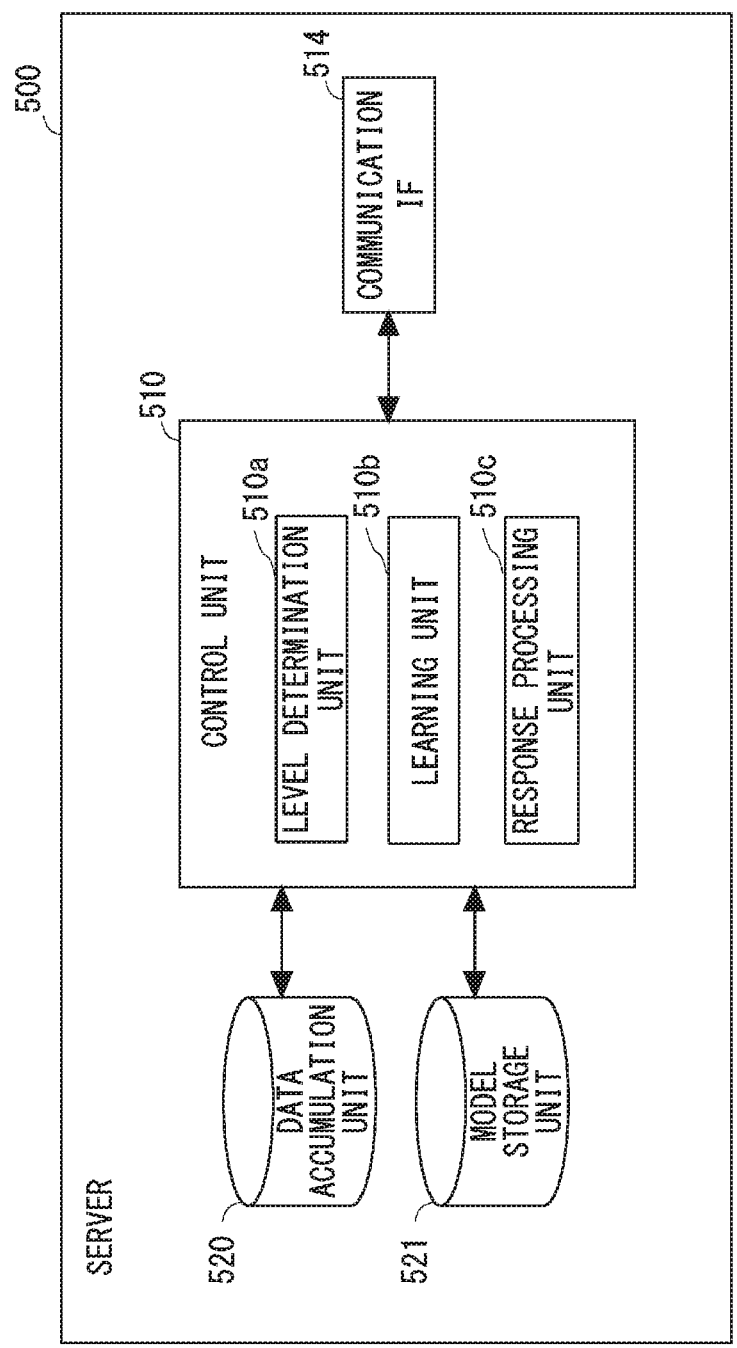
FIG. 4 is a block diagram showing a configuration of a server.

FIG. 4 is a block diagram showing an example of a configuration of the server 500. As shown in FIG. 4, the server 500 may include a control unit 510, a communication IF 514, a data accumulation unit 520, and a model storage unit 521. The control unit 510 is, for example, an MPU and controls the server 500 by executing a control program loaded from a system memory. The control unit 510 may include a data acquisition unit 510a, a learning unit 510b, and a response processing unit 510c, which will be described later. Further, in this case, the above-described control program includes a program(s) for implementing the functions of the aforementioned units 510a to 510c.

The communication IF 514 includes, for example, a wired LAN interface and is a communication interface for connecting to the network 400. The control unit 510 can receive profile data from the walking training apparatus 100 and transmit a processing result to the walking training apparatus 100 through the communication IF 514.

The data accumulation unit 520 includes a storage device such as an HDD (hard disk drive) or an SSD (solid state drive) and stores rehabilitation data therein. The control unit 510 writes the profile data received from the external communication apparatus 300 into the data accumulation unit 520 through the communication IF 514.

Similarly, the model storage unit 521 includes a storage device such as an HDD or an SSD. Note that the data accumulation unit 520 and the model storage unit 521 may include (i.e., share) a common storage device. When the server 500 performs a rehabilitation support process in cooperation with the walking training apparatus 100, at least an operable trained model is stored in the model storage unit 521.

The server 500 has a function as a learning apparatus for generating a trained model in addition to a function for outputting a recommended assistance level for the profile data received from the walking training apparatus 100. That is, the control unit 510 may be configured so as to perform control to switch between a function as a learning apparatus and a function for performing a rehabilitation support process by using a trained model. However, the server 500 may be distributed to (or divided into) an apparatus that is used in a learning stage and an apparatus that is used in an operation stage in which a trained model is used.

In the learning stage, the data acquisition unit 510a acquires the profile data and a selected assistance level that is an assistance level selected corresponding to this profile data. The data acquisition unit 510a acquires arbitrary profile data when the rehabilitation support processing is performed.

The learning unit 510b is provided to make the server 500 function as a learning apparatus, and the response processing unit 510c is provided to make the server 500 execute a part of the rehabilitation support processing.

The model storage unit 521 stores at least one of a learning model that has not been trained yet (including those under training) (hereinafter referred to as an untrained model) and a learning model that has been already trained (hereinafter referred to as a trained model). The server 500 serving as the learning apparatus is a processing apparatus for processing various data. For example, the server 500 performs machine learning using the acquired profile data and teacher data to generate a trained model. The learning apparatus may be referred to as a learning model generating apparatus. When the server 500 functions as a learning apparatus, at least an untrained model is stored in the model storage unit 521.

(Profile Data)

The profile data will be described here. The profile data acquired by the server 500 indicates information about the trainee, and includes at least one of the following types of information (1) to (5).

(1) Symptom Information of Disease that Trainee is Suffering from Symptom information may include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc. The symptom information may also include information indicating an initial symptom, a time when the symptom appears, and a current symptom in association with the above information. The symptom information may also include symptoms that are unlikely to be directly related to the rehabilitation in addition to the information indicating that the trainee needed to perform rehabilitation because of the symptoms included in the symptom information.

(2) Trainee's Cognitive Level Based on Functional Independence Measure

As a method for evaluating the trainee's cognitive level, for example, FIM (Functional Independence Measure) is known. The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

When the cognitive level of the trainee who performs a walking training is evaluated, a walking FIM is a general index indicating the degree of recovery. The walking FIM evaluates the cognitive level into seven stages from one point to seven points. For example, a patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee gradually increases.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a adjusting thickness, a used harness (e.g., with the walking assistance apparatus 120, with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

(3) Trainee's Assessment Score Based on Stroke Impairment Assessment Set

There is, for example, SIAS (Stroke Impairment Assessment Set) as an assessment method for quantifying an index for dysfunction caused by a stroke the trainee is suffering from. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

(4) Data Indicating the Trainee's Degree of Recovery

The data indicating a change in the above-described walking FIM can be data indicating the trainee's degree of recovery. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee is a hospitalized patient.

The data indicating the trainee's degree of recovery may be the Br. Stage (Brunnstrom Recovery Stage). The Br. Stage is an indicator of recovery in which a recovery process of a hemiplegia is divided into six stages based on the observation. In this embodiment, the data indicating the trainee's degree of recovery may include, of the Br. Stage, lower-limb items that are main items related to the walking training apparatus 100.

(5) Data Indicating Attributes of the Trainee

The data indicating attributes of the trainee include, for example, the trainee's age, sex, physique (height, weight, etc.), and a score indicating the trainee's physical condition.

Although the profile data has been described in detail above, the profile data is not limited to the above-described items. The profile data may include information of types different from those described above as long as it includes information satisfying the purpose of the profile data. The profile data may also include additional information such as a date and a time when the data is measured.

(Rehabilitation Data)

Next, the rehabilitation data will be described. The rehabilitation data may include setting parameters of the walking training apparatus 100, detection data detected by a sensor or the like provided in the walking training apparatus 100, and data regarding the training staff member 901 (hereinafter referred to as staff data).

The setting parameters of the walking training apparatus 100 include the assistance level of the walking assistance apparatus 120. Details of the assistance level will be described later. The detection data is data detected by a sensor or the like provided in the walking training apparatus 100. One specific example of the detection data is information about an angle detected by the angle sensor 223 of the walking assistance apparatus 120. The detection data also includes an output of each sensor included in the walking training apparatus 100.

The staff data indicates, for example, a property of the training staff member 901. The staff data includes a name or an ID, an age, a gender, a physique (a height, a weight, etc.) of the training staff member 901, a name of a hospital to which the training staff member 901 belongs, and his/her years of experience as a PT or a doctor. The staff data may include, as data related to the assistance, a value that numerically represents the timing at which the trainee 900 is assisted.

Further, in the case where a plurality of training staff members simultaneously assist the rehabilitation, the rehabilitation data may include data of the plurality of staff members. Further, each staff data may include information indicating whether the staff member is the main training staff member or an assistance training staff member. In addition to or instead of such information, each staff data may include information indicating whether the staff member is a training staff member who performs a setting operation and/or image checking in the management monitor 139, or whether or not the staff member is a training staff member who just physically supports the trainee 900 by hand.

(Assistance Level)

Next, the assistance level in this embodiment will be described in detail. In the walking training apparatus 100 according to this embodiment, when the trainee 900 performs a walking training, the walking assistance apparatus 120 assists the trainee to walk. More specifically, the walking assistance apparatus 120 assists an extending motion and a flexing motion of the knee of the diseased leg according to a walking cycle of the trainee.

Figure 5:
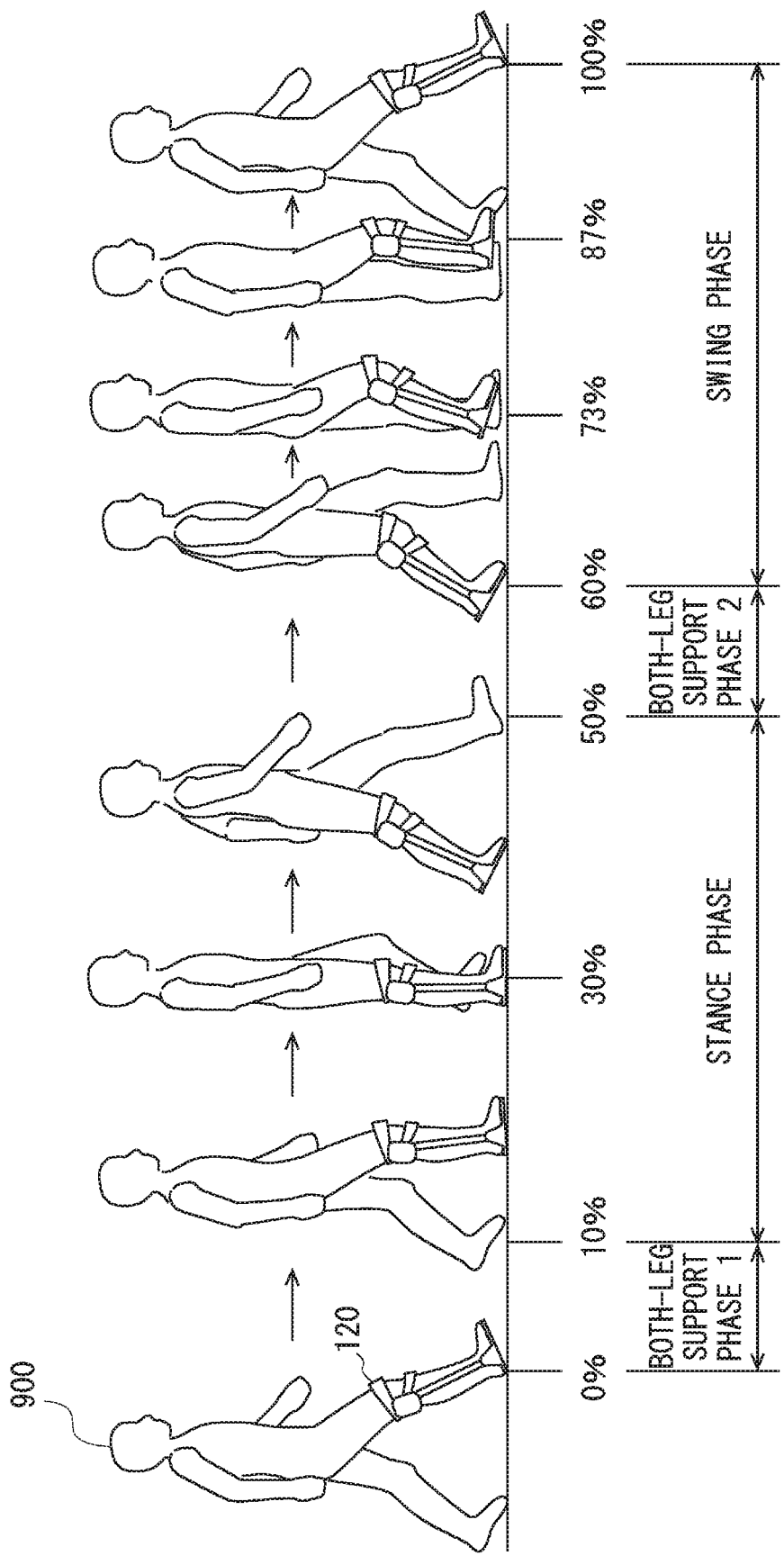
FIG. 5 shows an example of a walking cycle of a trainee.

The walking cycle of the trainee 900 will be described with reference to FIG. 5. FIG. 5 shows an example of the walking cycle of the trainee. FIG. 5 shows a walking trajectory for one cycle focusing on the right leg, which is the diseased leg of the trainee 900 walking from left to right. The walking trajectory is shown as 0% at a position where the right leg comes into contact with the floor surface, and 100% at a position where the right leg has walked for one cycle.

A walking cycle of one cycle is classified into 0 to 10% both-leg support phase 1, 10 to 50% stance phase, 50 to 60% both-leg support phase 2, and 60 to 100% swing phase. The both-leg support phase 1 is an initial stance phase, and the left leg, which is the leg opposite to the right leg, is also in contact with the floor surface. In the stance phase, the right leg (diseased leg), which is the leg of interest, comes into contact with the floor surface, and the left leg, which is the leg opposite to the right leg, is away from the floor surface. The both-leg support phase 2 is a terminal stance phase, and the left leg, which is the leg opposite to the right leg, also comes into contact with the floor surface. In the swing phase, the right leg, which is the leg of interest, is away from the floor surface.

The trainee 900 suffering from paralysis in the right leg may have difficulty supporting his/her weight during the stance phase of the walking cycle shown in the drawing. In such a case, the trainee 900's knee may greatly bend, resulting in "knee buckling". The knee buckling refers to a state in which, as the knee extension function deteriorates, the knee bends, and the trainee 900 cannot maintain the extending of his/her knee, and thus he/she unconsciously bends his/her knee while walking. Further, although the trainee 900 needs to extend his/her knee at the position around 30% of the walking cycle, he/she may not be able to extend his/her knee after bending his/her knee. Thus, the motor 121M of the control unit 121 is driven so as to prevent the knee from excessively bending or assist the knee to extend at a predetermined timing during the stance phase.

Figure 6:
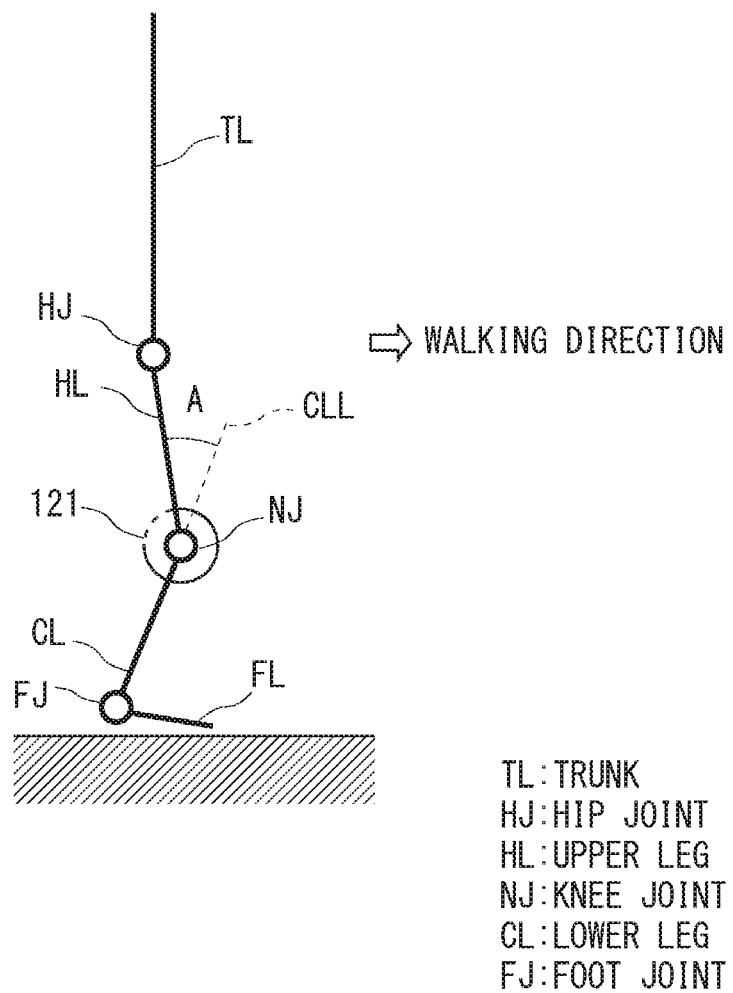
FIG. 6 shows an example of a knee extension angle of a diseased leg.

Next, an angle of the knee joint will be described with reference to FIG. 6. FIG. 6 shows an example of a knee extension angle of the diseased leg. FIG. 6 is a schematic diagram when the paralyzed body part, which is the lower body of the diseased leg, is observed from the side with respect to the walking direction. FIG. 6 shows a trunk TL, a hip joint HJ, an upper leg HL, a knee joint NJ, a lower leg CL, an ankle joint FJ, and a foot FL in order from the top. A lower leg extension line CLL is indicated by a dotted line as an extension line extending the lower leg CL upward. An angle between the upper leg HL and the lower-leg extension line CLL is shown as a knee extension angle A. In the schematic diagram of FIG. 6, the diseased leg of the trainee 900 is in the stance phase and is in contact with the floor surface.

The knee extension angle A of a healthy subject in the stance phase shown in the drawing is 10 to 15 degrees. Thus, the maximum knee extension angle A in the stance phase may be about 10 to 15 degrees even for the trainee 900 when he/she walks. However, when the trainee 900 cannot support his/her weight, the knee extension angle A may become much greater than 15. Thus, the motor 121M of the control unit 121 attached to the knee joint NJ is driven in a direction to return the knee extension angle A to within a predetermined range when the knee extension angle A exceeds a preset value.

Figure 7:
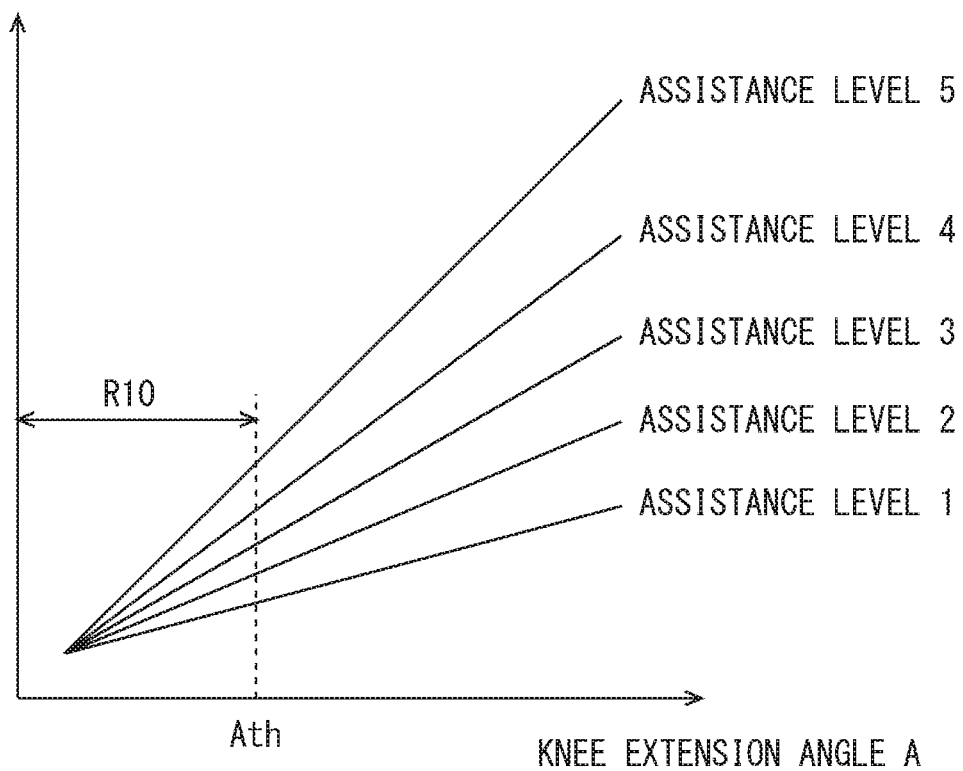
FIG. 7 is a first diagram showing an example of an assistance level.

Next, a relationship between the knee extension angle A and the torque of the motor 121M will be described with reference to FIG. 7. FIG. 7 is a first diagram showing an example of the assistance level. In the graph shown in the FIG. 7, the horizontal axis represents the knee extension angle A, and the vertical axis represents a torque T of the motor 121M. Solid straight lines plotted in the drawing indicate the assistance levels set in the motor 121M. In this embodiment, the assistance level is divided into 5 stages of 1 to 5.

The assistance levels are set such that the motor torque T increases as the knee extension angle A increases. In the example shown in this embodiment, the value of the motor torque T for the predetermined knee extension angle is the weakest at the assistance level 1 and the highest at the assistance level 5. Thus, the training staff member selects the assistance level 5, for example, for a trainee who needs strong assistance. The training staff member appropriately changes the assistance level according to the degree of recovery of the trainee.

A threshold Ath indicated by a dotted line in the drawing is set in the control unit 121. The threshold Ath is a threshold at which the motor 121M starts driving. That is, when the knee extension angle A exceeds the threshold Ath during the stance phase of the walking training, the motor 121M is driven to assist the knee extension operation. The motor torque T at the start of assisting the knee extension operation is determined by the set assistance level.

Figure 8:
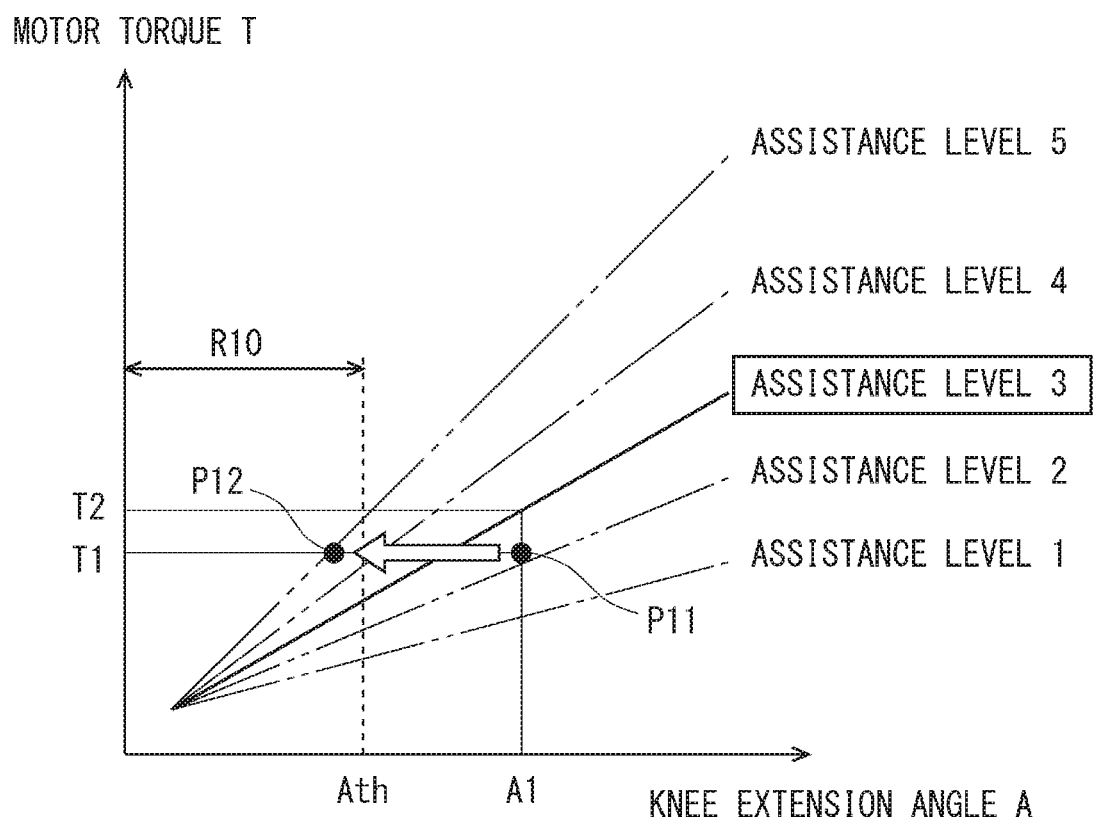
FIG. 8 is a second diagram showing an example of an assistance level.

A specific example of the assistance level will be described with reference to FIG. 8. FIG. 8 is a second diagram showing an example of the assistance level. The graph of FIG. 8 shows a state in which the assistance level 3 is selected at the time of walking training. Further, a point P11 shown in the drawing indicates that the knee extension angle of the diseased leg exceeds the threshold Ath and becomes an angle A1. In this case, the motor 121M assists an extending motion of the trainee 900's knee in such a way that the knee extension angle becomes smaller than the threshold Ath and fall within a range R10. A point P12 shown in the drawing indicates that the knee extension angle of the diseased leg assisted by the motor 121M becomes smaller than the threshold Ath.

A torque T1 shown in the drawing is a torque output by the motor 121M when it actually assists the diseased leg. A torque T2 shown in the drawing is a torque that the motor 121M with a setting of the assistance level 3 can output with the knee extension angle of the angle A1. In the example shown in the drawing, the motor 121M can be driven at the maximum torque T2 at the angle A1. However, it can be seen, from an observation of a transition from the point P11 to the point P12 plotted in the drawing, that the motor 121M can assist with the torque T1 in actuality. When the motor 121M is assisting with a torque lower than the maximum torque T2, this means that the trainee 900 is trying to extend his/her knee using his/her own power. That is, while the angle A1 of the trainee 900's diseased leg transitions within the range R10, a combined force of the trainee 900 and the motor 121M acts on the trainee's joint.

The assistance level of the assist performed by the motor 121M of the control unit 121 is set as described above. The threshold Ath may be a value slightly exceeding 15 degrees, for example, 20 degrees or 25 degrees. The walking training is preferably performed in such a way that the knee extension angle A falls within the range R10 shown in the drawing. By providing assistance in such a way that the knee extension angle A will not exceed the range R10, the walking training apparatus 100 can provide proper training. Although it is described that there are five assistance levels, there may instead be two or more levels. The above-described threshold Ath may be appropriately changed according to the assist timing.

The assistance level has been described so far. In order to effectively perform walking training using the walking training apparatus 100, it is important to set an appropriate assistance level. For example, when the setting of the assistance level is too high, the trainee 900 depends too much on the assistance of the motor 121M to exert his/her own power. In such a case, the training exercise cannot be effective. However, when the assistance level is set too low, the trainee 900 may not be able to fully extend his/her knee. In this case, the trainee 900's motivation to do the training is lowered, or the possibility of the trainee 900 falling down while walking is increased. In order to prevent such a situation from occurring, the assistance level may be set to a level at which the minimum assistance needed by the trainee 900 to exert his/her own power is needed.

However, when the assistance level is set depending on a training staff member's skill, there is a possibility that a difference between assistance level settings may become greater according to each training staff member. For example, an experienced PT can set the assistance level to an appropriate level as described above. However, a less experienced training staff member may not be able to set the assistance level appropriately, resulting in an ineffective training. Thus, the rehabilitation support system according to this embodiment learns the data of the training set by the experienced PT, generates a trained model, and presents the assistance level using the generated trained model.

(Learning Stage)

Figure 9:
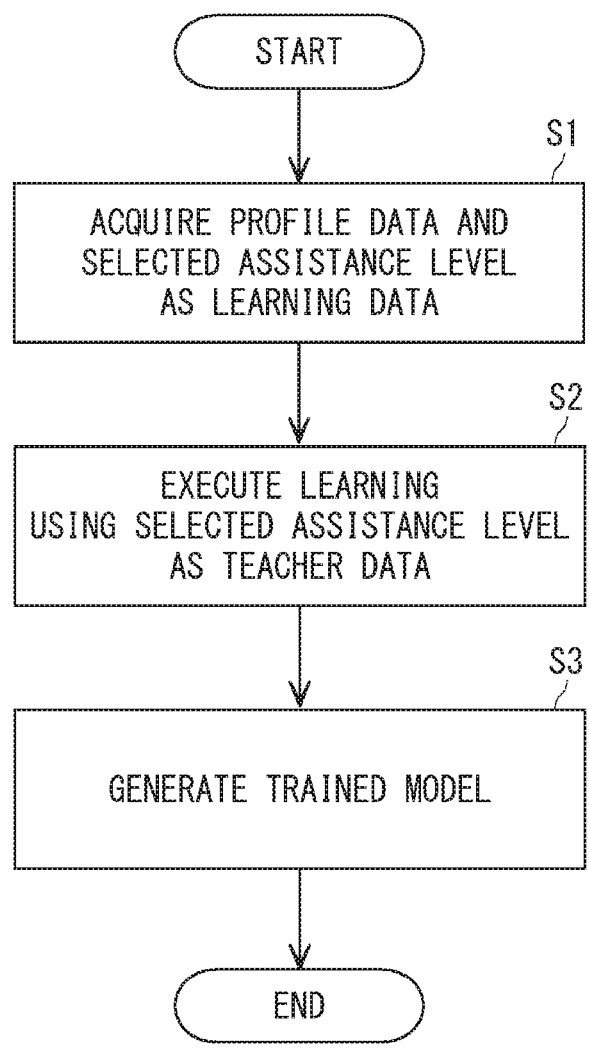
FIG. 9 is a flowchart for explaining an example of processes performed in a learning apparatus.

Next, the processing in the learning stage performed by the server 500 as the learning apparatus will be described with reference to FIG. 9. FIG. 9 is a flowchart for describing processing in the server 500, which is a learning apparatus.

First, the data acquisition unit 510*a* of the server 500 acquires the profile data and the selected assistance level as learning data (step S1). That is, when the server 500 performs learning, the selected assistance level corresponding to the profile data and the acquired profile data becomes one set of learning data.

As described above, the profile data includes at least one of the following data: symptom information of the disease that the trainee is suffering from; a cognitive level based on the functional independence measure; an assessment score based on the stroke impairment assessment set; an exercise ability level based on the exercise ability evaluation; information indicating the degree of recovery; and attribute data of the trainee. The selected assistance level is an assistance level selected in the training performed corresponding to the acquired profile data. The selected assistance level acquired by the server 500 is selected when the experienced PT configures an effective training.

Next, the learning unit 510*b* of the server 500 applies the acquired profile data to an input layer, and executes learning with the corresponding selected assistance level as the teacher data (step S2). Next, the learning unit 510*b* generates a trained model updated by the executed learning (step S3). The trained model refers to a learning model at a stage where the learning model updated by the above processing can be operable.

FIG. 10 is a table showing an example of data input to the learning apparatus. In the table shown in the drawing, the numbers in the left column are data set numbers (1,2,3 . . . ). The column to the right of the data set number is the data (2, 1, 7 . . . ) of the walking FIM as a parameter 1 applied to the input layer. The column to the right of the walking FIM is SIAS data (3, 2, 6 . . . ) as a parameter 2. The column to the right of SIAS is disease type data (cerebral infarction 2, cerebral hemorrhage 3, cerebral infarction 1 . . . ) as a parameter 3. In the disease type data, the numerical value assigned to the disease name indicates a more specific type in each disease, for example, the severity of the disease. The disease type may be a brain disease of the trainee, and the information about the type of disease may be information according to a location of brain damage causing the brain disease. The column to the right of the disease type is recovery history data (C, A, F . . . ) as a parameter 4. The column to the right of the recovery history data indicates the assistance level (2, 5, 1 . . . ) as the teacher data.

As described above, the data input to the learning apparatus includes a plurality of parameters applied to the input layer and the teacher data applied to the output layer. By performing the learning using such a plurality of data sets, the server 500, which is a learning apparatus, causes the learning unit 510*b* to learn. By using the above-mentioned learning data, the learning unit 510*b* learns to determine the recommended assistance level, which is the assistance level of the assistance apparatus recommended to be selected when the trainee uses the rehabilitation support system.

Note that the type of the learning model to be trained and its algorithm are not limited to any particular types and algorithms. However, a neural network can be used as the algorithm and, in particular, a deep neural network (DNN) using multiple hidden layers may be used. As the DNN, for example, a feedforward (forward propagation type) neural network such as a multilayer perceptron (MLP) employing an error back propagation method can be used.

Examples of input parameters input to the untrained model in the learning unit 510*b* and output parameters output from the untrained model will be described hereinafter by using an example in which the learning unit 510*b* generates a trained model by using the MLP. Each of the input parameters corresponds to a respective one of nodes in the input layer and each of the output parameters corresponds to a respective one of nodes in the output layer (i.e., objective variables). Note that an untrained model (untrained learning model) includes not only a completely untrained model but also a model under a learning process.

Figure 11:
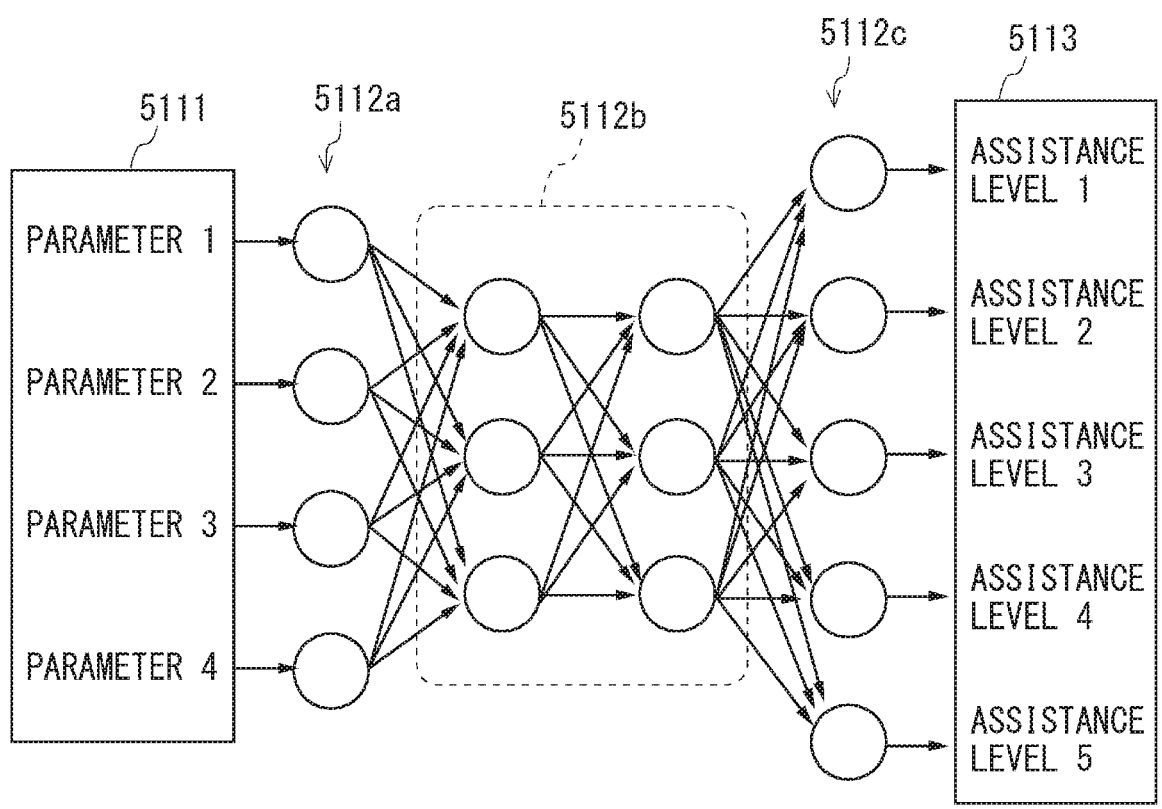
FIG. 11 shows an example of a learning model.

FIG. 11 shows an example of a learning model. FIG. 11 shows a learning model 5110. The learning model 5110 includes an input layer 5112a, an intermediate layer 5112b (also referred to as a hidden layer), and an output layer 5112c. The intermediate layer 5112b is provided between the input layer 5112a and the output layer 5112c.

The input layer 5112a includes a plurality of nodes, and receives data included in the data set. The intermediate layer 5112b includes a plurality of nodes. Note that the number of nodes and the number of hidden layers in the intermediate layer shown in the drawing are only examples, and the number of nodes and the number of layers are not limited to those shown in the drawing.

The output layer 5112c outputs a value for determining the recommended assistance level. In this embodiment, the output layer includes 5 nodes respectively corresponding to the assistance levels 1 to 5. When an objective function 5111 is input, the learning model 5110 outputs a predetermined numerical value to the output layer 5112c. The output of the output layer 5112c is compared with the teacher data 5113, and a result of the comparison is fed back. The learning model 5110 updates the threshold, weighting and the like in the learning model by repeating this processing.

Next, the learning unit 510b generates a trained model updated by the performed learning (step S3). The trained model indicates a learning model at a stage where the learning model updated by the above processing becomes operable.

By the above processing, the server 500 as the learning apparatus generates a trained model for outputting the recommended assistance level. Then, the rehabilitation support system can present a recommended assistance level when walking training is performed by using the generated trained model.

The learning unit 510b may use a neural network having a recursive structure such as RNN (Recurrent Neural Network) as the learning model in addition to the above-described configuration. The RNN may also be a neural network (sometimes simply referred to as LSTM) extended to include LSTM (Long short-term memory) blocks. In addition to the above configuration, the learning unit 510b may use a k-nearest neighbor algorithm (kNN).

(Operation Stage)

Figure 12:
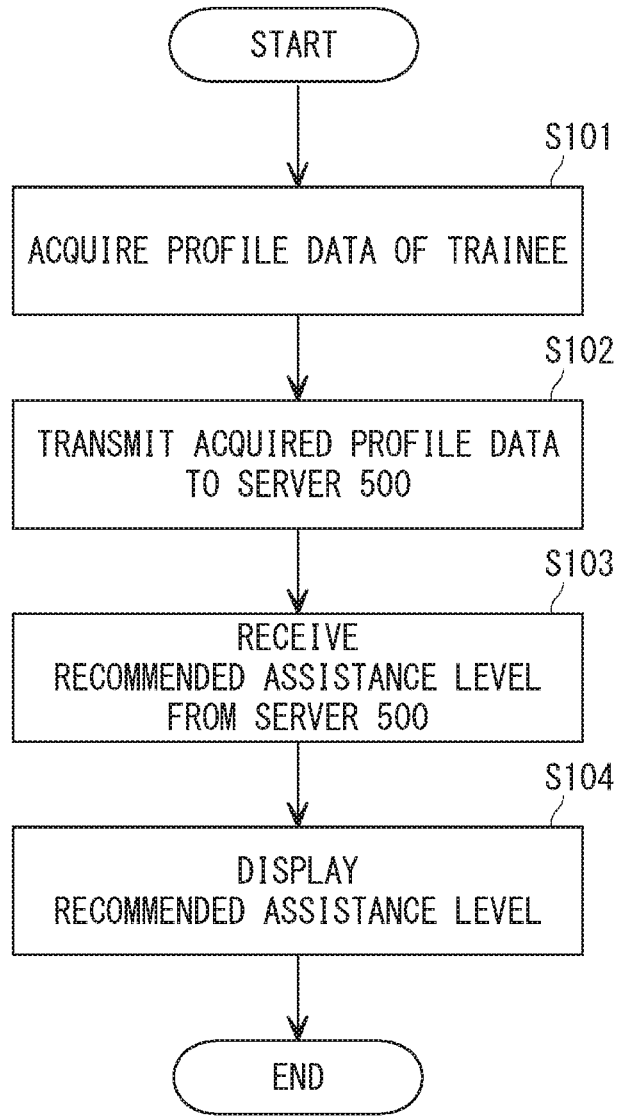
FIG. 12 is a flowchart for explaining an example of processes of the server.

Next, processing performed by the walking training apparatus 100 in the operation stage will be described with reference to FIG. 12. An operation stage is a stage in which rehabilitation is performed using the trained model generated by the learning apparatus. FIG. 12 is a flowchart for explaining an example of the processing of the server. As described above, the walking training apparatus 100 can use the trained model by accessing the server 500. At the operation stage, mainly the walking training apparatus 100 and the server 500 connected to the walking training apparatus through a network cooperate with each other as a rehabilitation support system, and rehabilitation support processing is performed.

First, the walking training apparatus 100 acquires profile data of a trainee (step S101). More specifically, the walking training apparatus 100 receives the profile data input by a PT or the like. The input of the profile data by the PT or the like is achieved, for example, by the overall control unit 210 controlling the display control unit 213 to cooperate with the operation reception unit 212.

Next, the walking training apparatus 100 transmits the acquired profile data to the server 500 through the network 400 (step S102). In the server 500 which has received the profile data from the walking training apparatus 100, the response processing unit 510c of the control unit 510 receives the profile data through the communication IF 514. The control unit 510 inputs the received profile data to the trained model stored in the model storage unit 521. The trained model outputs a recommended assistance level from the input profile data. The response processing unit 510c transmits the recommended assistance level output from the learning model to the walking training apparatus 100 through the communication IF 514.

Next, the walking training apparatus 100 receives the recommended assistance level from the server 500 (step S103). The walking training apparatus 100 displays the received recommended assistance level on the management monitor 139 (step S104).

By such processing, the walking training apparatus 100 can display the recommended assistance level corresponding to the received profile data. The PT can set the displayed recommended assistance level as an assistance level to be applied by the walking assistance apparatus 120. With such a configuration, the walking training apparatus 100 can appropriately set the assistance level regardless of the experience or intuition of the PT.

Although the embodiment has been described above, the walking training apparatus 100 according to the embodiment is not limited to the above-described configuration. For example, the walking training apparatus 100 may include a storage unit for storing a trained model or a processing unit for performing predetermined processing using the trained model. In this case, the walking training apparatus 100 outputs the profile data of the trainee to the processing unit as an input to the trained model, and notifies the trainee or the training staff member of the recommended assistance level output from the trained model as a response to the profile data. The walking training apparatus 100 according to the embodiment may be referred to as a rehabilitation support apparatus.

As described above, the walking training apparatus 100 outputs the trainee's profile data to the processing unit as an input to the trained model, and notifies the trainee or training staff member of the recommended assistance level output from the trained model in response to the profile data. The walking training apparatus 100 for executing the operation method of the rehabilitation support apparatus may be referred to as a rehabilitation support system. In this case, the walking training apparatus 100 may implement a part of the method described above in cooperation with an external server.

According to the above-described embodiment, it is possible to provide a learning apparatus or the like for setting an appropriate assistance level. Further, by utilizing the trained model generated by the learning apparatus, the rehabilitation support apparatus or the rehabilitation support system can notify the training staff member such as the PT of the recommended assistance level of the trainee performing rehabilitation. Thus, the rehabilitation support system according to the embodiment can output the recommended assistance level suitable for the untrained profile data.

The above-described program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (Read Only Memory), CD-R, CD-R/W, and semiconductor memories (such as mask ROM, PROM (Programmable ROM), EPROM (Erasable PROM), flash ROM, RAM (Random Access Memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Note that the present disclosure is not limited to the above-described embodiment, and may be appropriately modified without departing from the spirit and scope thereof. For example, the learning apparatus and the rehabilitation support system described above can be applied to a system for performing an assistance operation of the ankle or hip joint of the trainee in place of or in addition to the assist operation of the knee joint of the trainee. The learning apparatus and the rehabilitation support system described above can also be applied to a rehabilitation support system for training the movement of the arm instead of walking training.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A learning apparatus comprising a program that, when executed, causes a server to:
acquire, regarding rehabilitation executed using a rehabilitation support system including an assistance apparatus for assisting a motion of a trainee, profile data indicating a profile related to the trainee before the execution of the rehabilitation and a selected assistance level as learning data, the selected assistance level being an assistance level of the assistance apparatus selected at the time of the execution of the rehabilitation when a trainer configures an effective training;
learn to determine a recommended assistance level, the recommended assistance level being the assistance level of the assistance apparatus recommended to be selected when the trainee uses the rehabilitation support system based on the learning data, and to generate a trained model for receiving the profile data and outputting the recommended assistance level based on the learning; and
cause the assistance apparatus to set the assistance level of the trainee based on the recommended assistance level.

2. The learning apparatus according to claim 1, wherein the program further causes the server to:
perform the learning by using the profile data as an input and the selected assistance level as teacher data.

3. The learning apparatus according to claim 1, wherein the program further causes the server to:
acquire, as the profile data, at least one item of data of: symptom information of a disease the trainee is suffering from; a cognitive level based on a functional independence measure of the trainee; an assessment score based on a stroke impairment assessment set of the trainee; an exercise ability level based on an exercise ability evaluation of the trainee; information indicating the trainee's degree of recovery; and attribute data of the trainee.

4. The learning apparatus according to claim 3, wherein a type of the disease included in the profile data is a brain disease of the trainee, and information related to the type of the disease is information corresponding to a part of a brain damaged by the brain disease.

5. The learning apparatus according to claim 1, wherein the assistance apparatus is a motor for assisting the trainee to walk, and the assistance level is an index indicating a magnitude of a torque of the motor.

6. The learning apparatus according to claim 1, wherein the assistance apparatus is a motor for assisting an extending motion of a knee joint of the trainee, and the assistance level is an index indicating a magnitude of a torque of the motor with respect to a magnitude of an angle of the knee joint.

7. A rehabilitation support system capable of accessing a trained model that is a learning model generated by the learning apparatus according to claim 1, the rehabilitation support system comprising a microprocessor configured to:
output the profile data of the trainee as an input to the trained model; and
notify a user of the rehabilitation support system of the recommended assistance level output from the trained model as a response to the input profile data.

8. The rehabilitation support system according to claim 7, further comprising a server apparatus communicably connected to the rehabilitation support system, wherein
the server apparatus comprises a storage configured to store the trained model.

9. The learning apparatus according to claim 1, wherein the trained model generated by the learning apparatus causes a computer to function in such a way that the recommended assistance level is output based on the profile data of the trainee.

10. A learning method comprising:
acquiring, regarding rehabilitation executed using a rehabilitation support system including an assistance apparatus for assisting a motion of a trainee, profile data indicating a profile related to the trainee before the execution of the rehabilitation and a selected assistance level, the selected assistance level being an assistance level of the assistance apparatus selected at the time of the execution of the rehabilitation when a trainer configures an effective training;
learning to determine a recommended assistance level, the recommended assistance level being the assistance level of the assistance apparatus recommended to be selected when the trainee uses the rehabilitation support system based on the profile data and the selected assistance level, and to generate a trained model for receiving the profile data and outputting the recommended assistance level based on the learning; and
causing the assistance apparatus to set the assistance level of the trainee based on the recommended assistance level.

11. A rehabilitation support method capable of accessing the trained model that is a learning model learned by the learning method according to claim 10, the rehabilitation support method comprising:
outputting the profile data of the trainee who uses the rehabilitation support system as an input to the trained model; and notifying a user of the rehabilitation support system of the recommended assistance level output from the trained model as a response to the input profile data.

12. A non-transitory computer readable medium storing a learning program that causes a computer to execute a learning method comprising:

acquiring, regarding rehabilitation executed using a rehabilitation support system including an assistance apparatus for assisting a motion of a trainee, profile data indicating a profile related to the trainee before the execution of the rehabilitation and a selected assistance level, the selected assistance level being an assistance level of the assistance apparatus selected at the time of the execution of the rehabilitation when a trainer configures an effective training;

learning to determine a recommended assistance level, the recommended assistance level being the assistance level of the assistance apparatus recommended to be selected when the trainee uses the rehabilitation support system based on the profile data and the selected assistance level, and to generate a trained model for receiving the profile data and outputting the recommended assistance level based on the learning; and causing the assistance apparatus to set the assistance level of the trainee based on the recommended assistance level.

* * * * *